US005759539A

United States Patent [19]
Whitmire

[11] Patent Number: 5,759,539
[45] Date of Patent: Jun. 2, 1998

[54] METHOD FOR RAPID ENZYMATIC ALCOHOL REMOVAL

[75] Inventor: David R. Whitmire, Watkinsville, Ga.

[73] Assignee: Georgia Research Foundation, Inc., Athens, Ga.

[21] Appl. No.: 470,738

[22] Filed: Jun. 6, 1995

[51] Int. Cl.$^6$ ............................................. A61K 38/44
[52] U.S. Cl. ..................... 424/94.3; 424/94.2; 424/94.4
[58] Field of Search .......................... 424/94.2, 94.3, 424/94.4

[56] References Cited

U.S. PATENT DOCUMENTS

| | | | |
|---|---|---|---|
| 2,730,456 | 1/1956 | Green et al. | 117/36 |
| 2,730,457 | 1/1956 | Green et al. | 117/36 |
| 2,800,457 | 7/1957 | Green et al. | 252/316 |
| 3,625,214 | 12/1971 | Higuchi et al. | 128/260 |
| 4,272,398 | 6/1981 | Jaffe | 252/316 |
| 4,310,554 | 1/1982 | Olson et al. | 426/40 |
| 4,431,428 | 2/1984 | Schmer | 604/897 |
| 4,798,734 | 1/1989 | Kaneda | 426/565 |
| 4,906,474 | 3/1990 | Langer et al. | 424/428 |
| 4,925,673 | 5/1990 | Steiner et al. | 424/455 |
| 5,302,400 | 4/1994 | Sipos | 424/494 |

FOREIGN PATENT DOCUMENTS

| | | |
|---|---|---|
| 0398935 | 8/1994 | European Pat. Off. . |
| 0458745 | 9/1994 | European Pat. Off. . |
| WO 93/21906 | 11/1993 | WIPO . |

OTHER PUBLICATIONS

Whitmire, Dissertation Abstracts International 51(11-B):5453 (1988).

Whitmire et al., Alcoholism: Clinical and Experimental Research 15(5):804–807 (Oct. 1991).

Ameyama and Adachi, "[76] Alcohol Dehydrogenase from Acetic Acid Bacteria, Membrane–Bound," Methods in Enzymology 89:450–457 (1982).

Ameyama and Adachi, "[82] Aldehyde Dehydrogenase from Acetic Acid Bacteria, Membrane–Bound," Methods in Enzymology 89:491 (1982).

Armstrong, et al. Assessment of Myocardial Perfusion Abnormalities with Contrast–enhanced Two–dimensional Echocardiography 66:166–173 (1982).

Benita, et al. "Characterization of Drug–Loaded Ploy(d,–lactide) Microsphers,": J. Pharm Sci. 73: 1721–1724 (1984).

Bostian and Betts, "Rapid Purification and Properties of Potassium–Activated Aldehyde Dehydrogenase from Saccharomyces Cerevisiae," Biochemical Journal, 173: 773–786 (1978).

Buhner, M., and Sund H., "Yeast Alcohol Dehydrogenase:— SH Groups, Disulfide Groups, Quaternary Structure, and Reactivation by Reductive Cleavage of Disulfide Groups," European Journal of Biochemistry 11:73–79 (1969).

*Commander, J. C. M.S. thesis from Auburn University, Alabama,* (1980) see also Microencapsulation and Related Drug Processes, pp. 61–193 (Dekker, 1984).

Deasy, Patrick, Microencapsulation and Related Drug Processes, pp. 61–193 (Dekker, 1984).

Feinstein, et al., "Two–Dimensional contrast Echocardiography. 1. In Vitro Development and Quantitative Analysis of Echo Contrast Agents," J. Am. Coll. Cardiol 3: 14–20 (1984).

Gillam, et al. "Functional and Pathologic Effects of Multiple Echocardiographic Contrast Injections on the Myocardium, Brian and Kidney," J. Am Coll. Cardiol, 6:687–694 (1985).

Gregoriadis, G. Chapter 14 ("Liposomes") Drug Carriers in Biology and Medicine, pp. 287–341 (Academic Press, 1979).

Ireton–Jones, et al., "Doses the Use of an Enteral Feeding Tube with a pH Sensitive Tip Facilitate Enteral Nutrition?" J. Burn Care Rehabilitation 14(2, pt 1):215–217 (1993).

Jalil and Nixon, "Biodegradable poly(lactic acid)and poly-(lactide–co–glycolide)Microcapsules: Problems Associated with Preparative Techniques and Release Properties," J. Microencapsulation 7:297–325 (1990).

(List continued on next page.)

Primary Examiner—Jean C. Witz
Attorney, Agent, or Firm—Arnall Golden Gregory, LLP

[57] ABSTRACT

A method and formulations have been developed to accelerate ethanol elimination from the body, which combine enzymes that oxidize alcohol to acetate, enzymes which regenerate NADH to NAD, substrates which are rate limiting for the requisite enzymes, buffering agents which protect the enzymes against pH variations (e.g. low gastric pH), gastric acid sequestrants which block synthesis of gastric acid, protease inhibiting agents and other agents which protect the enzymes against proteolysis, carbohydrates which protect labile enzymes against bile salt inactivation, and a source of oxygen for efficient catalysis by some of the enzymes, with a packaging for delivery of a functional enzyme system to an appropriate in vivo site for ethanol conversion to acetate. The oxygen source can be mechanical means, such as a tube or catheter which directs oxygen from a high pressure source into the upper gastrointestinal tract for the most rapid removal of ethanol from the blood as in the case where a patient has overdosed and is unconscious, a physical carrier of oxygen, for example, oxygen microencapsulated in an appropriate polymeric matrix, or an oxygen generating formulation such as catalase (one to ten million units) with hydrogen peroxide (0.1–200 grams), which is stable to passage through the stomach and releases oxygen in the gastrointestinal tract. The formulation is preferably administered orally, although it can also be packaged for administration in any surface through which rapid transport of ethanol from blood to the enzymes can occur. A preferred surface for rapid ethanol transport is mucosal membrane such as is found in the intestine or mouth.

21 Claims, 2 Drawing Sheets

OTHER PUBLICATIONS

Kemper, et al., "Hydrogen Peroxide Contrast Echocardiography: Quantification in vivo of Myocardial Risk Area During Coronary Occlusion and of the Necrotic Area Remaining After Myocardial Reperfusion," *Circulation* 70(2):309–317 (1984).

Lim, et al., "Microencapsulation of Living Cells and Tissues," *J. Pharm Sci.* 70:351–354 (1981).

Edward Majchrowicz *Biochemistry and Pharmacology of Ethanol* vol. I (Majchrowicz, ed., Plenum Press, N.Y. 2979).

Mathiowitz, et al. "Polyanhydride Microspheres as Drug Carriers. II. Microencapsulation by Solvent Removal," *Journal of Applied Polymer Science* 35(3):755–774 (1988).

Mathiowitz, et al., "Morphology of Polyanhydride Microsphere Delivery Systems," *Scanning Microscopy* 4:329–340 (1990).

Metheny, et al., "Effectiveness of pH Measurements in Predicting Feeding Tube Placement," *Nursing Research* 38(5):280–285 (1989).

Nakano, et al., "Sustained Urinary Excretion of Sulfamethizole Following Oral Administration of Enteric Coated Microcapsules in Humans," *Int. J. Pharm.* 4:29–298 (1980).

*Salib, et al., *Pharmazeutische Industrie* 40–11A, 1230 (1978).

Sawhney, et al., "Bioerodible Hydrogels Based on Photopolymerized Poly(ethylene glycol)–co–poly($\alpha$–hydroxy acid) Diacrylate Macromers," *Macromolecules* 26(No. 4):581–587 (1993).

Sefton, et al., "Ethylene–Vinyl Acetate Copolymer Microsphers for Controlled Release of Macromolecules," *J. Pharm. Sci.* 73(12):1859–1861 (1984).

Smith, et al., "Superior Intensity and Reproducibility of SHU–454, a New Right Heart Contrast Agent," *J. Am Coll. Cardiol* 3 (No. 4):992–998 (1984).

*Whitmire, D. R., "Multi Enzyme System with Substrate Pumped NAD Recyling Applied to Ethanol Detoxification of the Dog," Ph.D. dissertation.

METHOD FOR RAPID ENZYMATIC ALCOHOL REMOVAL

BACKGROUND OF THE INVENTION

This invention generally relates to methods and orally administered formulations for rapid removal of alcohol from individuals.

Alcohol abuse is a significant cause of accidents and death. Major alcohol related problems exist in almost every phase of human activity including recreation and the workplace. Chronic alcohol abuse leads to many serious disorders, most commonly liver cirrhosis. Twenty percent of emergency room visits in the United States, approximately 90 million visits, are alcohol related. Lethal blood ethanol concentrations are generally in the range of 0.25% and 1.50%. Ethanol overdose without complications leads to approximately 1000 deaths per year in the United States.

Ethanol is rapidly transported into the blood from the intestine, and is also transported into the blood from the stomach. Metabolism of ingested alcohol as measured by disappearance of ethanol from the blood, follows zero order kinetics above blood alcohol concentration (BAC) values of 2 mM. The linear rate of blood alcohol elimination is 2 to 5 mM/hour, accordingly, four to ten hours are required to remove most of the alcohol from the body.

As reviewed in *Biochemistry and Pharmacology of Ethanol*, vol. 1, (Majchrowicz, ed., Plenum Press, N.Y., 1979), ethanol is eliminated by respiration, excretion, and metabolism, ninety percent of which occurs in the liver. In general, liver alcohol dehydrogenase (LADH) metabolizes the majority of the ethanol. The alcohol metabolism rate is limited by the relatively low value of the LADH Michaelis constant (Km) and the NADH (nicotinamide adenine dinucleotide, reduced form) oxidation (regeneration) rate. The microsomal alcohol-oxidizing system (MAOS) located in microsomes of the smooth endoplasmic reticulum of hepatocytes is a second alcohol metabolism mechanism. This mechanism is dependent on regeneration of NADPH (nicotinamide adenine dinucleotide phosphate, reduced form). A third alcohol metabolizing mechanism depends on the enzyme catalase and hydrogen peroxide. This mechanism is thought to metabolize relatively little ethanol in vivo because of the need for hydrogen peroxide at the enzyme site. A gastric alcohol dehydrogenase present in stomach mucosa is a fourth alcohol metabolizing mechanism. The importance of this fourth mechanism of alcohol metabolism relative to the LADH mechanism is not clear at this time.

Only two methods are known to accelerate ethanol elimination from the body. Ingestion of fructose can increase the ethanol elimination rate by 0% to 25% greater than control values in some subjects. It is thought that fructose only increases NADH regeneration, thereby helping to maintain the LADH mechanism at its maximum intrinsic rate of ethanol metabolism. Dialysis of alcohol-containing blood using traditional kidney dialysis only slightly accelerates alcohol elimination.

In 1980, J. C. Commander published a M.S. thesis from Auburn University, Alabama, proposing that an enzyme system be used for the detoxification of alcohol. The study reported that ethanol diffused from the blood into the intestinal lumen when the blood ethanol concentration was greater than the intestinal ethanol concentration. Commander proposed using an enzyme system isolated from liver, which remains active in the intestine. Generally the intestinal lumen pH is 6.0 to 8.0 and 80% of ingested ethanol is absorbed into the blood from the intestinal lumen. The multi-enzyme system which he tested in vitro included buffer salts containing bovine serum albumin (BSA), potassium ions, thiol groups (e.g. β-2-mercaptoethanol), NAD, NADH, acetaldehyde, alcohol dehydrogenase, and aldehyde dehydrogenase (ALDH) in various concentration.

In 1988, D. R. Whitmire published as his Ph.D. dissertation "Multi Enzyme System with Substrate Pumped NAD Recycling Applied to Ethanol Detoxification of the Dog". This dissertation reported the development of a method using yeast alcohol dehydrogenase (YADH) and yeast aldehyde dehydrogenase (YALDH) in an appropriate buffer to oxidize alcohol to acetate using lactate dehydrogenase (LDH) catalyzed pyruvate pumped NAD recycling. A second system using a cell-free extract of *gluconobacter suboxydans* in an appropriate buffer was also developed and shown to oxidize ethanol. A third system using YADH, YALDH in combination with glycerol dehydrogenase (GDH) as the recycle enzyme was also described. Problems with gastric pH deactivation, proteolytic degradation, and bile salt inactivation of the enzymes were overcome using protease inhibitors, pepstatin, and a sucrose-phosphate-dithiothreitol buffer. However, in vivo use of these enzyme systems posed significant problems: The system had a high pyruvate requirement with is not normally present in the intestine in large quantities; sucrose buffer (50% w/v) was required to stabilize the YALDH against bile salt actions; pyruvate and lactate are univalent ions of salts which yield two moles of solute for each mole of salt; high sucrose concentration and high salt concentration caused the enzyme system to be hyperosmolar; and lactate produced by the recycling reaction can potentially lead to lactic acidosis. Accordingly, while this approach demonstrated the theoretical feasibility of using an orally administered formulation of enzymes to rapidly oxidize ethanol which exsorbed into the intestine, because of the significant problems enumerated above, it does not provide a practical, commercially acceptable means for accelerating ethanol elimination from the body.

It is therefore an object of the present invention to provide methods and compositions for accelerating ethanol elimination from the body.

It is another object of the present invention to provide methods and compositions which can be used with unconscious patients as well as for casual drinkers.

SUMMARY OF THE INVENTION

A method and formulations have been developed to accelerate ethanol elimination from the body, which combine enzymes that oxidize alcohol to acetate, enzymes which regenerate NADH to NAD, substrates which are rate limiting for the requisite enzymes, buffering agents which protect the enzymes against pH variations (e.g. low gastric pH), gastric acid sequestrants which block synthesis of gastric acid, protease inhibiting agents and other agents which protect the enzymes against proteolysis, carbohydrates which protect labile enzymes against bile salt inactivation, and a source of oxygen for efficient catalysis by some of the enzymes, with a packaging for delivery of a functional enzyme system to an appropriate in vivo site for ethanol conversion to acetate. The oxygen source can be mechanical means, such as a tube or catheter which directs oxygen from a high pressure source into the upper gastrointestinal tract for the most rapid removal of ethanol from the blood as in the case where a patient has overdosed and is unconscious, a physical carrier of oxygen, for example, oxygen microencapsulated in an appropriate polymeric matrix, or an oxygen generating formulation such as catalase (one to ten million units) with hydrogen peroxide (0.1–200 grams), which is stable to passage through the stomach and releases oxygen in the gastrointestinal tract.

The formulation is preferably administered orally, although it can also be packaged for administration in any surface through which rapid transport of ethanol from blood to the enzymes can occur. A preferred surface for rapid ethanol transport is mucosal membrane such as is found in the intestine or mouth.

DETAILED DESCRIPTION OF THE INVENTION

Figure 1:
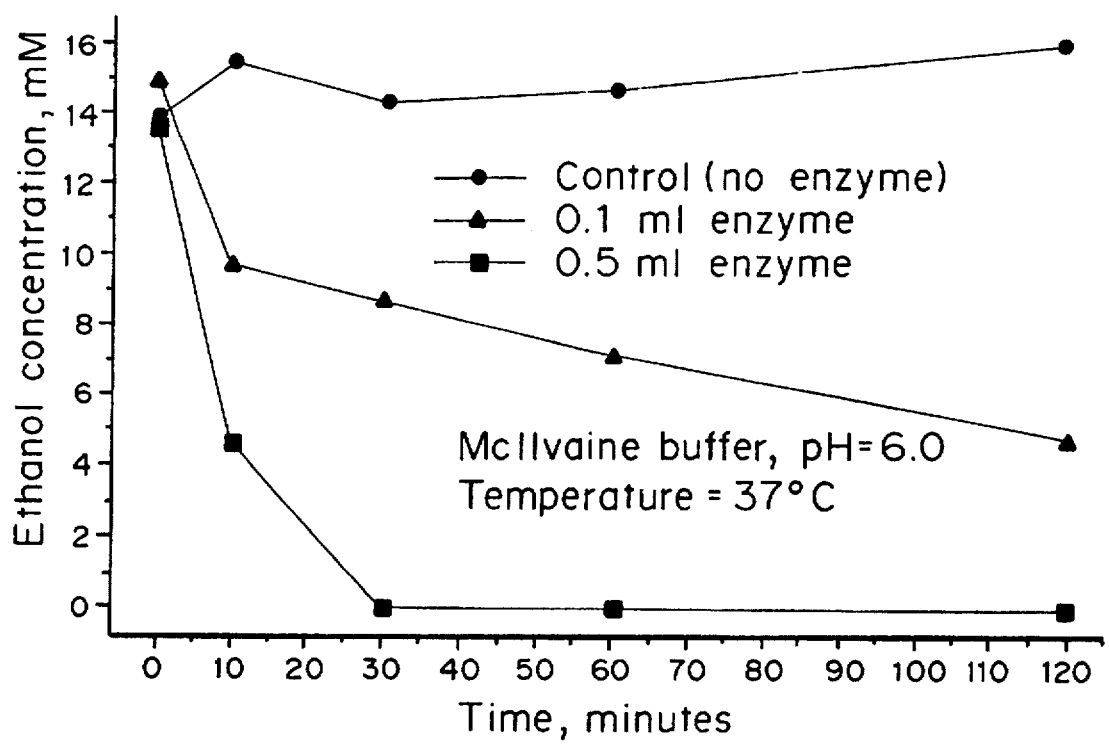
FIG. 1 is a graph of rapid ethanol lowering for a membrane fraction of *Gluconobacter oxydans* at pH 6.0, 37° C., shown as ethanol concentration (mM) over time (minutes), for control without enzyme (circles), 0.1 ml enzyme (triangles), and 0.5 ml enzyme (squares).

A method and formulations have been developed to accelerate ethanol elimination from the body, having the following components:

Enzymes: enzymes which oxidize alcohol to acetate, enzymes which regenerate NADH to NAD, Enzyme substrates which are rate limiting for the requisite enzymes, Agents which protect the enzymes against pH variations (and/or gastric acid sequestrants which block synthesis of gastric acid), and agents protecting the enzymes from proteolysis and bile salt inactivation, Oxygen source(s) for efficient catalysis by some of the enzymes, and Packaging for delivery of a functional enzyme system to an appropriate in vivo site for ethanol conversion to acetate.

I. Enzyme Systems

Enzyme catalysis

The enzyme catalyzed reactions required to remove ethanol from the blood are as follows:

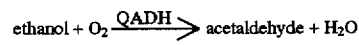

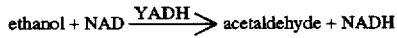

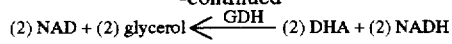

Enzymes

The enzymes used in this system include yeast alcohol dehydrogenase (YADH), enzyme commission number (E.C. 1.1.1.1), yeast aldehyde dehydrogenase (YALDH) (E.C. 1.2.1.3) and glycerol dehydrogenase (GDH) (E.C. 1.1.1.6), all of which are commercially available from a number of sources including Sigma Chemical Company, St. Louis, Mo., and quinoprotein alcohol dehydrogenase (QADH) (E.C. 1.1.99.8), and quinoprotein aldehyde dehydrogenase (QALDH) (E.C. 1.2.99.3) from *Gluconobacter suboxydans* or *Acetobacter suboxydans*, or *oxydans* either in purified form or obtained as cell extracts, as described in more detail below. The QADH and QALDH are activated by detergents such as bile salts and bile acids and use molecular oxygen ($O_2$) as an electron acceptor.

YADH. Yeast alcohol dehydrogenase can be obtained commercially from Sigma Chemical Company or other commercial other suppliers. Alternatively, a yeast extract containing YADH can be prepared using the procedure of Buhner, M., and Sund, H., *European Journal of Biochemistry* VOL. 11, P. 73, 1969.

YALDH. Yeast aldehyde dehydrogenase can be obtained commercially from Sigma Chemical Company or other commercial suppliers. Alternatively, a yeast extract containing YALDH can be prepared using the procedure of Bostian and Betts, *Biochemical Journal*, 173, 773 (1978).

GDH. Glycerol dehydrogenase can be obtained commercially from Sigma Chemical Company or other commercial suppliers.

Quinoprotein dehydrogenases. Quinoprotein alcohol dehydrogenase (QADH) can be obtained using the procedures of Ameyama and Adachi, "[76] Alcohol Dehydrogenase from Acetic Acid Bacteria, Membrane-Bound", in *Methods in Enzymology* (W. Wood, ed.), vol. 89, p. 450, 1982. Quinoprotein aldehyde dehydrogenase (QALDH) can be obtained using the procedures of Ameyama and Adachi, "[82] Aldehyde Dehydrogenase from Acetic Acid Bacteria, Membrane-Bound," in *Methods in Enzymology* (W. Wood ed.), vol. 89, p. 491, 1982.

Previous studies used alcohol dehydrogenase (YADH) and acetaldehyde dehydrogenase (YALDH) to catalyze ethanol and acetaldehyde oxidation respectively. YADH and YALDH are somewhat labile to detergents such as bile salts found in the gastrointestinal tract. It has now been determined that in some cases QADH and QALDH, which are activated by detergents such as bile salts in the gastrointestinal tract, are preferred. QADH and QALDH use molecular oxygen ($O_2$) as a terminal electron acceptor, eliminating the need to include NAD or NADH, which are required co-factors for YADH and YALDH.

The Gluconobacter enzymes require oxygen; the yeast enzymes do not. Accordingly, the enzymes can be used alone or in combination, depending on the application. For example, for a formulation designed to lower breath alcohol, the Gluconobacter enzymes alone may be used. Where oxygen is limited, a mixture or the yeast enzymes alone may be preferable.

Rate Limiting Substrates for Enzymes

DHA. Previous studies used lactic dehydrogenase (LDH) to catalyze the NADH–>NAD recycle reaction. It has now been determined that glycerol dehydrogenase is preferred in many cases, since the substrates for lactic dehydrogenase can be toxic. Use of GDH allows pyruvate salt, required by LDH as a recycling substrate, to be replaced with dihydroxyacetone (DHA), a three-carbon sugar-like compound, as a substrate. As a sugar, DHA can serve as a stabilizer of the enzymes in a manner similar to sucrose, as well as a GDH substrate for the recycle reaction. Replacement of sucrose and pyruvate by a single compound such as DHA significantly reduces the osmolarity of the multi-enzyme system. The end product of the preferred GDH-catalyzed recycle reaction is glycerol, which is less toxic than lactate. DHA can be obtained from commercial sources such as Sigma Chemical Co.

Other substrates can be selected based on the selection of enzymes, as described above. For example, if fructose dehydrogenase were to be used, the substrate would be fructose. In the case of gluconolactone dehydrogenase, gluconate can be used. These are not preferred due to the high osmolarity these substrates would create, however.

II. Excipients

Excipients, defined herein as stabilizers of enzyme activity, solubilizing agents which increase the solubility of the enzymes, release modifying agents, viscosity modifiers, matrix modifying agents and pH buffering agents, can be added to the formulation as appropriate to maximize the efficacy of the enzyme formulation.

Stabilizers

Enzyme stabilizers include carbohydrates, amino acids, fatty acids, and surfactants and are known to those skilled in the art. Stabilizers are based on a ratio to the protein on a weight basis. Examples include carbohydrates such as sucrose, lactose, mannitol, dextran, proteins such as heparin, albumin and protamine, amino acids such as, arginine, glycine, and threonine, surfactants such as bile salts, Tween® (detergent) and Pluronic (polyethylene oxide-polypropylene glycol block copolymers), salts such as calcium chloride and sodium phosphate, and lipids such as fatty acids, phospholipids, and bile salts. The ratios are generally between 1:10 and 4:1, carbohydrate to protein, amino acids to protein, protein stabilizer to protein, and salts to protein: between 1:1000 and 1:20, surfactant to protein; and between 1:20 and 4:1, lipids to protein.

Release Rate Modifiers

In those cases where the enzyme formulation is administered in a polymeric matrix, excipients which modify the solubility of the enzymes such as salts and complexing agents (albumin, protamine) can be used to control the release rate of the protein from a matrix. Agents which enhance degradation of the matrix or release from the matrix can also be incorporated. They can be added to the enzymes, added as a separate phase (i.e., as particulates), or can be codissolved in the polymer phase depending on the compound. In all cases the amount should be between 0.1 and thirty percent (w/w polymer). Types of degradation enhancers include inorganic salts such as ammonium sulfate and ammonium chloride, organic acids such as citric acid, benzoic acid, and ascorbic acid, inorganic bases such as sodium carbonate, potassium carbonate, calcium carbonate, zinc carbonate, and zinc hydroxide, and organic bases such as protamine sulfate, spermine, choline, ethanolamine, diethanolamine, and triethanolamine and surfactants such as Tween® and Pluronic®.

Pore forming agents which add microstructure to the matrices (i.e., water soluble compounds such as inorganic salts and sugars) are added as particulates. The range should be between one and thirty percent (w/w polymer).

Buffering Agents.

pH of the formulation is important. Suitable buffering agents include acetate buffers, 2-amino-2-methyl-1-propanol, glycine buffers, phosphate buffers, (tris [hydroxymethyl]aminomethane) (TRIS) buffers, (2-[N-morpholino]ethanesulfonic acid) (MES), Bis-Tris, (N-[2-acetamido]-2-iminodiacetic acid; N-[carbamoylmethyl] iminodiacetic acid) (ADA), (2-[(2-amino-2-oxoethyl) amino]ethanesulfonic acid; N-[2-acetamido]-2-aminoethanesulfonic acid) (ACES), (piperazine-N,N'-bis[2-ethanesulfonic acid]; 1,4-piperazinediethanesulfonic acid) (PIPES), (3-[N-morpholino]-2-hydroxypropanesulfonic acid) (MOPSO), Bis-Tris Propane, (N,N-bis[2-hydroxyethyl]-2-aminoethanesulfonic acid; 2-[bis(2-hydroxyethyl)aminoethanesulfonic acid; 2-[bis(2-hydroxyethyl)amino]ethanesulfonic acid (BES), (3-[N-morpholino]propanesulfonic acid) (MOPS), (N-tris [hydroxymethyl]methyl-2-aminoethane-sulfonic acid; 2-( [2-hydroxy-1, 1-bis(hydroxymethyl)ethyl]amino) ethanesulfonic acid (TES), (N-[2-hydroxyethyl)piperazine-N'[2-ethanesulfonic acid) (HEPES), (3-[N,N-bis(2-hydroxyethyl)amino]-2-hydroxy-propanesulfonic acid) (DIPSO), (3-[N-tris(hydroxymethyl)methylamino]-2-hydrooxypropanesulfonic acid) (TAPSO), (N-[2-hydroxyethyl]piperazine-N'-[2-hydroxypropanesulfonic acid) (HEPPSO), (POPSO), (N-[2-hydroxyethyl)piperazine-N'-[3-propasesulfonic acid] (EPPS), triethanolamine (TEA), (N-tris[hydroxymethyl]methylglycine; N-[2-hydroxy-1,1-bis(hydroxymethyl)ethyl]glycine) (Tricine), (N,N-bis[2-hydroxyethyl]glycine) (Bicine), (N-tris[hydroxymethyl] methyl-3-aminopropanesulfonic acid; ([2-dhyroxy-1,1-bis (hydroxymethyl)-ethyl]amino)-1-propanesulfonic acid) (TAPS), (3-[(1,1-dimethyl-2-hydroxyethyl)amino]-2-hydroxypropanesulfonic acid) (AMPSO), (2-[N-cyclohexylamino]ethanesulfonic acid) (CHES), (3-[cyclohexylamino]-2-hydroxy-1-propanesulfonic acid) (CAPSO), 2-amino-2-methyl-1-propanol (AMP), and (3-[cyclohexylamino]-1-propanesulfonic acid) (CAPS), among others. These are available from commercial sources such as Sigma Chemical Co.

Protease Inhibitors.

Since the enzymes are degraded by proteases in the person to whom the enzyme formulation is administered, it is important to add protease inhibitors to the formulation. Suitable protease inhibitors include amastatin, nitrobestatin, antipain, α1-antitrypsin, aprotinin, bestatin, cystatin, chymostatin, 3,4-dichloroisocournarin, ehelactone A, ebelactone B, elastinal, trans-epoxysuccinyl-L-leucylamido-(4-guanidino)butane (E-64), calcium chelating agents such as ethylenediamine tetraacetic acid (EDTA) and ethylene glycol-bis(amino ethyle ether) N,N,N',N'-tetraacetic acid (EGTA), leupeptin, Nle-Sta-Ala-Sta, pepstatin A, phenylmethylsulfonyl fluoride (PMSF), N-(α-rhamnopyrranosyloxyhydroxy-phosphinyl-Leu-Trp (phosphoramidon), N-p-lysine chloromethyl ketone (TLCK), N-toxyl-L-phenylalanine chloromethyl ketone (TPCK), trypsin inhibitor (soybean), and trypsin inhibitor (egg), available from Sigma Chemical Co., St. Louis, Mo., and other commercial suppliers.

Gastric Acid Inhibitors.

Many gastric acid inhibitors are known, for example, famotidine. These are used to treat ulcer patients.

III. Preferred Enzyme Formulations

The essential elements of the formulations are the enzymes and rate limiting substrate. Oxygen is also essential when the gluconobacter enzymes are utilized. Although preferred, protease inhibitors, gastric acid inhibitors, and buffering agents can be omitted through the use of appropriate carriers, such as the polymeric carriers described below.

A preferred mixture for oral administration of acute alcohol toxicity is 2.18 g $K_2HPO_4$, 0.2 g glutathione, 0.25 g NAD, 28,000 units YADH, 56,000 units YALDH, 84,000 units GDH, 100 mg aprotinin, 40 mg famotidine, 180 g DHA, HCl to pH 8.0, in a total volume of 300 ml. Famotidine, N'-[aminosulfonyl]-3-[(2-[diaminomethyleneamino]-4-thiazolyl)methylthio]-propanamidine).

Ranges of these materials include between one and ten g $K_2HPO_4$, 0.1 to 1 g glutathione, 0.1 to 1 g NAD, at least 1000 to 1,000,000 units YADH, at least 1000 to 1,000,000 units YALDH, at least 1000 to 1,000,000 units GDH, one to 1000 mg protease inhibitor, 1 to 100 mg gastric acid inhibitor, 180 to 500 g DHA, in a total volume of 300 ml.

A second preferred mixture oral administration is 2.18 g $K_2HPO_4$, 0.2 g glutathione, 28,000 units QADH, 56,000 units QALDH, 100 mg aprotinin, 40 mg famotidine, and 1.848 moles oxygen ($O_2$), in a total volume of 300 ml.

Ranges of these materials include between one and 10 g $K_2HPO_4$, 0.1 to 1 g glutathione, at least 1000 to 1,000,000 units QADH, at least 1000 to 1,000,000 units QALDH, 1 to 1000 mg protease inhibitor, 1 to 100 mg famotidine, and 0.1 to 10 moles oxygen ($O_2$).

Since the enzymes are catalysts, the reaction rate is dependent on the amount of enzyme. The more enzyme, the faster the rate, if sufficient substrate is present. Accordingly, ranges are described as "at least", since more enzyme can be used.

IV. Oxygen sources

Mechanical Means such as Catheters.

Nasogastric catheters, such as the Accusite® pH enteral feeding system, sold by Zinetics Medical, Salt Lake City, Utah, can be used to direct oxygen into the small intestine where the pH increases from values typical of the gastric environment (pH between 1.0 and approximately 4.0) to values typical of the duodenum and small intestine (pH between 4.0 and approximately 9.0). Location of the tube can be verified by pH measurements or radio-graphic examination, for example, as reviewed by Metheny, et al, *Nursing Research* 38(5), 280–285 (1989), Ireton-Jones, et al, *J. Burn Care Rehabilitation* 14(2, pt 1), 215–217 (1993).

Microencapsulated Oxygen.

As used herein, microencapsulated oxygen refers to air, alone or in combination with other gases, oxygen generators, or oxygen carriers, in a formulation delivering the gas to the small intestine, and includes emulsions, liposomes, polymeric microparticles, microspheres, and microcapsules. Systems which release oxygen immediately upon reaching the small intestine are preferred. To maximize reaction rate, oxygen should be provided in a ratio of 2 moles oxygen for each mole of ethanol to be oxidized. Since blood alcohol is approximately 0.1%, or 40 g (approximately 1 mole of ethanol) in an intoxicated individual, two moles of oxygen (approximately 64 g) is required to oxidize all ethanol in the body. A casual user may have a blood alcohol level less than 0.1 %.

Microencapsulated Gases.

As described in more detail below, air or oxygen can be encapsulated and/or emulsified in a suitable carrier for oral, buccal or rectal administration to a patient. Emulsions of air and viscous solutions such as 70% sorbitol and 50% dextros are described by Feinstein et al., *J. Am. Coll. Cardiol* 3, 14–20 (1984), Smith et al., *J. Am. Coll. Cardiol*, 3, 992–998 (1984), Gillam et al., *J. Am. Coll. Cardinol*, 6, 687–694 (1985), Kemper et al., *Circulation*, 70, 309–317(1984), and Armstrong et al., *Circulation* 66, 166–173(1982).

Microbubbles containing air have been formulated from albumin and are marketed by Molecular Biosystems, Inc., San Diego, Calif. for use in ultrasound imaging. European Patent Application No. 89730021.6 (EP 0,398,935) SCHERING AKTIENGESELLSCHAFT and European Patent Application No. 91810366.4 (EP 0458 745) by SINTETICA S.A. describe the encapsulation of air in synthetic polymetric microbubbles. The Liposome Company has developed a lipid based emulsion of air for use in imaging. Oxygen can also be entrapped in capsules formed of an enteric material which releases upon reaching the small intestine, using coating materials such as those described in Deasy (1984).

Oxygen carriers. An oxygen carrier such as the perfluorocarbon blood substitutes developed and marketed by Green Cross (Osaka, Japan) can also be used, to supplement or replace the carrier.

Oxygen generators. Compounds which generate oxygen can be used instead of, or in addition to, oxygen carriers. Examples include enzymes (such as catalase) and peroxyacids. Hydrogen peroxide, for example, could be encapsulated in an enteric coating for release within the small intestine. The amount of hydrogen peroxide solution required depends upon the concentration used, but at least 200 ml is necessary to oxidize all of the ethanol in the water in a person.

V. Delivery Formulations.

The enzymes, rate limiting substrate, stabilizers and protective agents, are administered in combination. The oxygen source can be administered in combination with the enzyme formulation or separately, either simultaneous with administration of the enzyme formulation or separately, for example, by catheter. A preferred site for administration is a mucosal membrane, due to much higher transfer rates present due to the relatively higher degree of vascularization and permeability of mucosal membranes as compared with skin.

The enzyme formulation is administered orally or locally to a mucosal membrane in the mouth, nasopharyngeal region, or rectum, using formulations as described above. A variety of materials are known which can be used to encapsulate and protect the enzymes and to provide a source of oxygen, as described above. These can be a number of small microparticles (inclusing microspheres and microcapsules) which are formulated in an appropriate liquid carrier or encapsulated within a larger enteric coating for release in the small intestine. A variety of known materials are stable to passage through the stomach, i.e. low pH, which then erode and release the drug upon reaching the higher pH of the small intestine.

Oral Formulations. Oral formulations can consist of an enzyme suspension, solution, or emulsion, incorporating buffers, stabilizers, protease inhibitors, substrate, and recycle substrate as well as flavorings, colorings, and viscosity-modifying agents (sugars, polysaccharides such as alginate, and others are well known and approved for food and drug use). These can be encapsulated and ingested as tablets or liquids. Administration to the mouth as a lozenge or chewing gum will also reduce alcohol within exhaled alveolar air, thus reducing alcohol-odor from breath.

Formulations for buccal or rectal administration. For administration to a mucosal membrane such as those found in the mouth, rectum, or nasopharyngeal area, it may not be necessary to provide an enteric coating. The formulation can be prepared as a porous hydrogel or other material which allows for free diffusion of ethanol and ethanol metabolites into and out of the material, while retaining the enzymes within the formulation. This can be achieved by immobilization of the enzymes to the material or through the use of a selectively porous material. Also, bioadhesive microspheres which can adhere to mucosal membranes and increase drug retention time to the body are known to those skilled in the art and are discussed, for example, in PCT/US93/03822 by Brown University.

Microparticle preparation

Liposomes and Emulsions. Liposomes consist of a phospholipid bilayer which forms a shell around an aqueous core. Methods for preparing liposomes for administration to a patient are known to those skilled in the art; for example, U.S. Pat. No. 4,798,734 describes methods for encapsulation of biological materials in liposomes. The biological material is dissolved in a aqueous solution, and the appropriate phospholipids and lipids are added, along with surfactants if required. The material is then dialyzed or sonicated, as necessary. A review of known methods is presented by G. Gregoriadis, Chapter 14 ("Liposomes"), in *Drug Carriers in Biology and Medicine*, pp. 287–341 (Academic Press, 1979).

Polymeric Microparticles. Microspheres formed of polymers or proteins are also well known to those skilled in the art, and can be tailored for passage through the gastrointestinal tract, as described in U.S. Pat. Nos. 4,906,474, 4,925,673, and 3,625,214, for example. There are a number of well-known methods, including solvent evaporation and coacervation/phase separation, for preparing microspheres.

Bioerodible microspheres can be prepared using any of the methods developed for making microspheres for drug delivery, as described, for example, by Mathiowitz et al., *J. Appl. Polymer Sci.* 35, 755–774(1988), and P. Deasy, in *Microencapsulation and Related Drug Processes*, pp. 61–193, (Dekker, 1984), the teachings of which are incorporated herein. The selection of a method depends on the drug properties and choice of polymer, as well as the size, external morphology, and degree of crystallinity desired, as discussed, for example, by Benita et al., *J. Pharm. Sci.* 73, 1721–1724 (1984), Jalil and Nixon, *J. Microencapsulation*, 7, 297–325(1990), and Mathiowitz et al., *Scanning Microscopy* 4, 329–340(1990), the teachings of which are incorporated herein.

In solvent evaporation, described, for example, in Mathiowitz et al., (1990), Benita, and U.S. Pat. No. 4,272,398 to Jaffe, the polymer is dissolved in a volatile organic solvent. The drug, either in soluble or particulate form, is added to the polymer solution and the mixture is suspended in an aqueous phase containing a surface active agent such as poly(vinyl alcohol). The resulting emulsion is stirred until most of the organic solvent evaporates, leaving solid microspheres. Microspheres of various sizes (1–1000 microns) and morphologies may be obtained by this method, which is useful for non-labile polymers.

Coacervation/phase separation techniques have been used to encapsulate both solid and liquid core materials with various polymer coatings. U.S. Pat. Nos. 2,730,456,2,730,457, and 2,800,457 to Green and Schleichter, describe gelatin and gelatin-acacia (gum arabic) coating systems, for example. Simple coacervation employs a single colloid (e.g. gelatin in water) and involves the removal of the associated water from around the dispersed colloid by agents with a higher affinity for water, such as alcohols and salts. Complex coacervation employs more than one colloid, and the separation proceeds mainly by charge neutralization of the colloids carrying opposite charges rather than by dehydration. Coacervation may also be induced using nonaqueous vehicles, as described in Nakano et al., *Int. J. Pharm*, 4, 29–298(1980), for example.

Hydrogel microspheres made of gel-type polmers such as alginate or polyphosphazines or other dicarboxylic polymers can be prepared by dissolving the polymer in an aqueous solution, suspending the material to be incorporated into the mixture, and extruding the polymer mixture through a microdroplet forming device, equipped with a nitrogen gas jet. The resulting microspheres fall into a slowly stirring, ionic hardening bath, as illustrated, for example, by Salib, et al., *Pharmazeutische Industrie* 40-11A, 1230(1978), the teachings of which are incorporated herein. The advantage of this system is the ability to further modify the surface of the microspheres by coating them with polycationic polymers (such as polylysine) after fabrication, as described, for example, by Lim et al., *J. Pharm Sci.* 70, 351–354(1981). The microsphere particle size depends upon the extruder size as well as the polymer and gas flow rates.

Examples of polymers that can be used include polyamides, polycarbonates, polyalkylenes and derivatives thereof including, polyalkylene glycols, polyalkylene oxides, polyalklylene terepthalates, polymers of acrylic and methacrylic esters, including poly(methyl methacrylate), poly(ethyl methacrylate), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate), polyvinyl polymers including polyvinyl alcohols, polyvinyl ethers, polyvinyl esters, polyvinyl halides, poly(vinyl acetate), and polyvinylpyrrolidone, polyglycolides, polysiloxanes, polyurethanes and co-polymers thereof, celluloses including alkyl cellulose, hydroxyalkyl celluloses, cellulose ethers, cellulose esters, nitro celluloses, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, and cellulose sulphate sodium salt, polypropylene, polyethylenes including poly(ethylene glycol), poly(ethylene oxide), and poly(ethylene terephthalate), and polystyrene.

Examples of biodegradable polymers include synthetic polymers such as polymers of lactic acid and glycolic acid, polyanhydrides, poly(ortho)esters, polyurethanes, poly(butic acid), poly(valeric acid), and poly(lactide-co-caprolactone), and natural polymers such as alginate and other polysaccharides including dextran and cellulose, collagen, chemical derivatives thereof (substitutions, additions of chemical groups, for example, alkyl, alkylene, hydroxylations, oxidations, and other modifications routinely made by those skilled in the art), albumin and other hydrophilic proteins, zein and other prolamines and hydrophobic proteins, copolymers and mixtures thereof. In general, these materials degrade either by enzymatic hydrolysis or exposure to water in vivo, by surface or bulk erosion. Bioadhesive polymers of particular interest include bioerodible hydrogels described by H. S. Sawhney, C. P. Pathak and J. A. Hubell in *Macromolecules*, 1993, 26, 581–587, the teachings of which are incorporated herein, polyhyaluronic acids, casein, gelatin, glutin, polyanhydrides, polyacrylic acid, alginate, chitosan, poly(methyl methacrylates), poly(ethyl methacrylates), poly(butylmethacrylate), poly(isobutyl methacrylate), poly(hexyhnethacrylate), poly(isodecyl methacrylate), poly (lauryl methacrylate), poly(phenyl methacrylate), poly(methyl acrylate), poly(isopropyl acrylate), poly(isobutyl acrylate), and poly(octadecyl acrylate).

In a preferred embodiment, the enzyme system is encapsulated into ethylenevinyl acetate microcapsules of 1 to 2 mm in diameter, prepared according to the method of Sefton et al., *J. Pharm. Sci.* 73(12), 1859–1861(1984). Buffer salts consisting of mono and di basic sodium phosphate to yield pH 7.8 are included in the polymer solution during synthesis to yield loadings up to 50%, preferably between 20 and 40%. Large biological molecules such as proteins and enzymes can be added to between zero and 50% loading, with a preferred loading of 20%.

VI. Pharmaceutical administration

The enzyme formulations are designed to be administered either by the person desiring to lower their blood alcohol or the alcohol content in their breadth, under non-critical conditions, or by hospital or emergency personnel when the person to be treated is unconcious. In the latter case, the oxygen is preferrably administered via catheter, in order to increase the rate of the reaction.

As noted above, the dosage is determined from the alcohol level to be decreased. In all cases, an excess can be used. The amount of rate limiting substrate and oxygen are determinative of the dosage of enzyme to be used. The preferred ratio is 2:1, substrate to alcohol.

The present invention will be further understood by reference to the following non-limiting examples.

EXAMPLE 1: IN VITRO LOWERING OF ETHANOL USING A *GLUCONOBACTER OXYDANS* MEMBRANE PREPARATION

*Gluconbacter suboxydans* membrane fractions containing enzyme are prepared as described by Ameyama and Adachi, in "Alcohol Dehydrogenase from Acetic Acid Bacteria, Membrane-Bound" in *Methods in Enzymology* vol. 89, Carbohydrate Metabolism Part D, ed. W. A. Wood (Academic Press, NY 1982), the teachings of which are incorporated by reference herein. Basically, bacteria are cultured using standard culture methods, the cells are suspened in 0.1 M buffer and homogenized using a French press (American Instrument Co.) at 100 k/cm$^2$, then the suspension centrifuged to remove intact cells. The membrane fraction is suspended in 10% Triton X-100, 2-mercaptoethanol, 0.01 M buffer, pH 6.0, then centrifuged after an overnight incubation. The solubilized enzyme is precipitated using polyethylene glycol 6000 added to 20%, dialyzed into 0.01 M buffer, and chromatographed on DEAE-Sephadex A-50, eluted with 0.002 M buffer containing 0.1% Triton X-100. The eluted enzyme is then chromatographed on DEAE-Sephadex A-50 using a linear gradient of 0.015 and 0.1 M phosphate buffer and 0.05% Triton X-100. The enzyme is then rechromatographed on hydroxyapatite equilibrated in 0.01 M buffer contaoning 0.1% Triton X-100 eluted stepwise with 0.02 M, 0.05 M and 0.1 M buffer containing 0.1% Triton X-100. Activity elutes in the 0.1 M buffer.

Ethanol degradation by the enzyme formulation was determined for samples containing 0.1 ml enzyme, 0.5 ml enzyme, and no enzyme, as a function of time, in McIlvaine buffer, pH 6.0 at 37° C., for 14 mM ethanol.

The results are shown in FIG. 1. 0.5 ml of enzyme was effective in decreasing the ethanol concentration from 14 mM to 4 mM in ten minutes at a pH of 6.0 and a temperature of 37° C. The level was decreased to 0 mM within 30 minutes.

EXAMPLE 2: IN VITRO LOWERING OF ETHANOL CONCENTRATION USING ADH IN COMBINATION WITH ALDH AND DHA AS THE RATE LIMITING SUBSTRATE.

Degradation of ethanol by a system using ADH and ALDH was measured, comparing different concentrations of enzymes over time. Samples contained 1 mM NAD, 250 units GDH, in a phosphate buffer at pH 7.8, at a temperature of 37° C, and either no enzyme (control), 40 u ADH and 20 u ALDH, 20 u ADH and 10 u ALDH, or 10 ADH and 5 ALDH.

Figure 2:
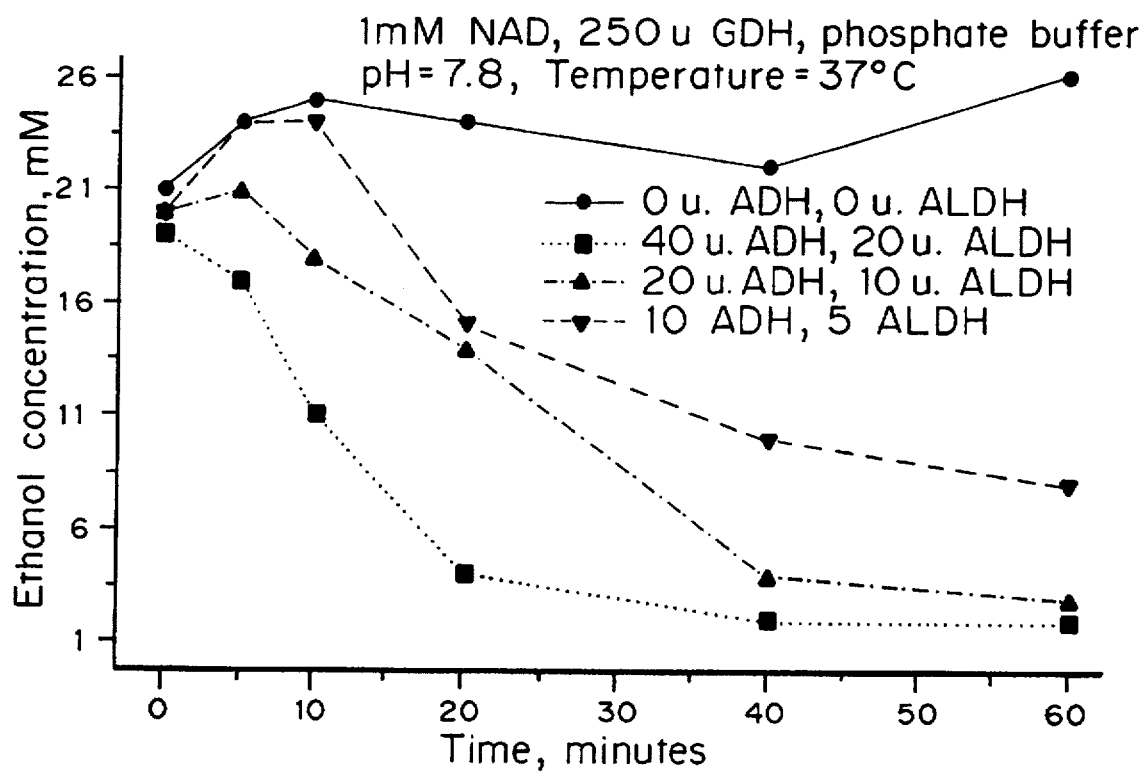
FIG. 2 is a graph of rapid ethanol lowering with DHA pumped NAD recycling at pH 7.8, 37° C., shown as ethanol concentration (mM) over time (minutes), for 0 units alcohol dehydrogenase (ADH) and 0 units aldehyde dehydrogenase (ALDH) (circles), 40 units ADH+20 units ALDH (squares), 20 units ADH+10 units ALDH (triangle), 10 ADH+5 ALDH (inverted triangle).

The results with DHA pumped NAD recycling are shown in FIG. 2. The rate of ethanol removal was proportional to the amount of enzyme present in the reaction mixture. Using 40 units of ADH in combination with 20 units of ALDH, ethanol concentration was decreased from 21 mM to 5 mM in 20 minutes and to approximately 1 mM within 40 minutes. Similar decreases in ethanol concentrations were achieved within 40 minutes using 20 units ADH and 10 units ALDH.

Figure 3:
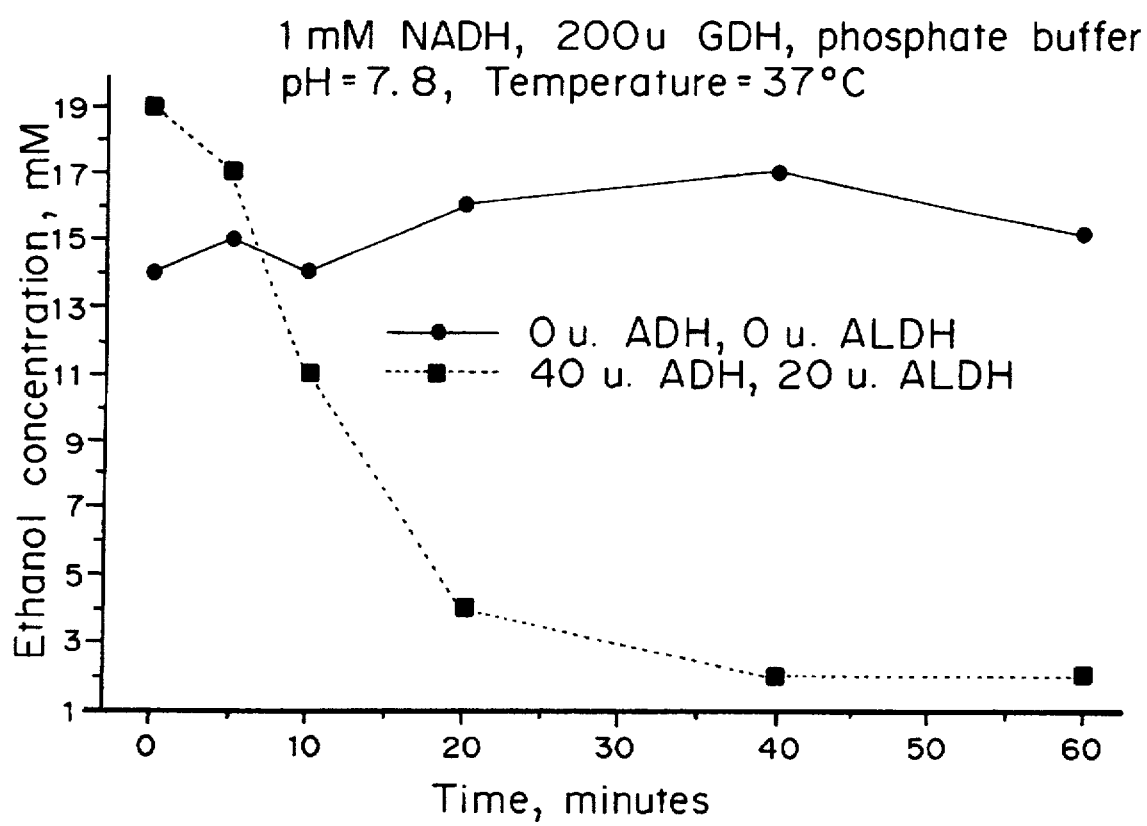
FIG. 3 is a graph of rapid ethanol lowering with DHA pumped NADH recycling with 1 mM NADH, 200 u GDH, phosphate buffer pH 7.8, 37° C., ethanol concentration (mM) over time (minutes), 0 units ADH+0 units ALDH, 40 units ADH, 20 units ALDH.

The results with DHA pumped NADH recycling using 1 mM NADH and 20 u GDH, 40 u ADH and 20 u ALDH are shown in FIG. 3. Ethanol concentration was decreased from 19 mM to less than 5 mM within 20 minutes using 40 units ADH and 20 units ALDH. This demonstrates that the enzyme effectively recycles the NADH back to NAD.

Modifications and variations of the present invention will be obvious to those skilled in the art and are intended to come within the scope of the appended claims.

I claim:

1. A method for making a formulation to lower blood alcohol comprising providing in combination quinoptotein alcohol dehydrogenase (QADH) and quinoprotein aldehyde dehydrogenase (QALDH) from *Glucanobacter suboxydans* or *Acetobacter suboxydans* or *oxydans*, either in purified form or as cell extracts, in an amount effective to metabolize ethanol, protective agents selected from the group consisting of pH buffering compounds, gastric acid sequestrants, protease inhibitors, enteric coatings, and polymeric matrices, in an amount effective to preserve the enzyme activity after administration to a patient, a pharmaceutically acceptable carrier for the enzymes in combination with the protective agents, and a source of oxygen in an amount sufficient for the enzymes to metabolize ethanol after administration to a patient.

2. The method of claim 1 further comprising adding to the formulation yeast alcohol dehydrogenase (YADH), yeast aldehyde dehydrogenase (YALDH), and yeast glycerol dehydrogenase (GDH).

3. The method of claim 1 wherein the oxygen source is a catheter for delivery of oxygen to the stomach or upper portion of the small intestine, further comprising administering the formulation to a patient in need thereof and delivering oxygen to the stomach or upper portion of the small intestine.

4. The method of claim 1 wherein the oxygen is provided in a delivery means selected from the group consisting of liposomes, emulsions, and microparticles.

5. The method of claim 1 wherein the oxygen source is a compound generating oxygen at the site where ethanol is to be metabolized.

6. The method of claim 1 wherein the oxygen source is a compound binding oxygen.

7. The method of claim 1 wherein the enzymes and protective agents are packaged into polymeric microparticles.

8. The method of claim 2 wherein the formulation further comprises dihydroxyacetone.

9. A formulation to lower blood alcohol comprising quinoprotein alcohol dehydrogenase (QADH) and quinoprotein aldehvde dehvdrogenase (QALDH) from *Glu-*

*canobacter suboxydans* or *Acetobacter suboxydans* or *oxydans*, either in purified form or as cell extracts, in an amount effective to metabolize ethanol, a pharmaceutically acceptable carrier for administration of an effective amount of the enzymes to a person to decrease the blood level of alcohol, and a source of oxygen in an amount sufficient to metabolize ethanol after the formulation is administered to a person in need of treatment thereof.

10. The formulation of claim 9 further comprising yeast alcohol dehydrogenase (YADH), yeast aldehyde dehydrogenase (YALDH), and yeast glycerol dehydrogenase (GDH), either in purified form or as cell extracts, in an amount effective to metabolize ethanol.

11. The formulation of claim 9 wherein the carrier comprises protective agents selected from the group consisting of pH buffering compounds, gastric acid sequestrants, and protease inhibitors, in an amount effective to preserve the enzyme activity after administration to a patient, and a pharmaceutically acceptable carrier for the enzymes in combination with the protective agents.

12. The formulation of claim 9 wherein the oxygen source is a catheter for delivery of oxygen to the stomach or upper portion of the small intestine.

13. The formulation of claim 9 wherein the oxygen is provided in a delivery means selected from the group consisting of liposomes, emulsions, and microparticles.

14. The formulation of claim 9 wherein the oxygen source is a compound generating oxygen at the site where ethanol is to be metabolized.

15. The formulation of claim 9 wherein the oxygen source is a compound binding oxygen.

16. The formulation of claim 11 wherein the enzymes and protective agents are packaged into microparticles.

17. The formulation of claim 9 for oral administration to treat acute alcohol toxicity comprising between one and 10 g $K_2HPO_4$, 0.1 to 1 g glutathione, at least 1000 to 1,000,000 units QADH, at least 1000 to 1,000,000 units QALDH, 1 to 1000 mg protease inhibitor, 1 to 100 mg famotidine, and 0.1 to 10 moles oxygen ($O_2$).

18. The formulation of claim 17 comprsing 2.18 g $K_2HPO_4$, 0.2 g glutathione, 28,000 units QADH, 56,000 units QALDH, 100 mg aprotinin, 40 mg famotidine, 1.848 moles oxygen ($O_2$).

19. The formulation of claim 9 where the carrier is for administration buccally.

20. The formulation of claim 9 where the carrier is for rectal administration.

21. The formulation of claim 9 where the carrier is for oral administration to the gastrointestinal tract.

* * * * *